United States Patent [19]

Adams et al.

[11] Patent Number: 5,466,934
[45] Date of Patent: Nov. 14, 1995

[54] METHOD AND APPARATUS FOR IDENTIFICATION OF CRYSTALLOGRAPHIC DEFECTS

[76] Inventors: Brent L. Adams, 3808 Kim La., Gibsonia, Pa. 15044; David J. Dingley, 4099 S. 550 East #15F, Salt Lake City, Utah 84107; David P. Field, 628 E. 630 North, Pleasant Grove, Utah 84062

[21] Appl. No.: 374,214

[22] Filed: Jan. 18, 1995

[51] Int. Cl.[6] .................................................. G01N 23/203
[52] U.S. Cl. ............................................. 250/307; 250/310
[58] Field of Search ........................................ 250/307, 310

[56] References Cited

U.S. PATENT DOCUMENTS

| | | | |
|---|---|---|---|
| 4,952,804 | 8/1990 | Nakagawa et al. | 250/307 |
| 4,990,779 | 2/1991 | Yoshitomi et al. | 250/307 |

OTHER PUBLICATIONS

Etingof and Adams; Jun. 6, 1992; Representations of Polycrystalline Microstructure by n–Point Correlation Tensors.
Wright; 1993; A Review of Automated Orientation Imaging Microscopy (OIM)[1].
Adams, Wright and Kunze; Apr. 1993; Orientation Imaging: The Emergence of a New Microscopy.
Brent L. Adams; 1993; Orientation Imaging Microscopy: Application to the Measurement of Grain Boundary Structure.

*Primary Examiner*—Jack I. Berman
*Attorney, Agent, or Firm*—Lowell W. Gresham; Jordan M. Meschkow

[57] ABSTRACT

An imaging apparatus (10) includes a scanning electron microscope (12) which is controlled to bombard numerous points (62) of a material sample (24) with an electron beam (18). Backscatter diffraction patterns are collected by an image collection system (26) which may include both a slower responding video camera (32) and a faster responding diode array (40). For a baseline point (62), an electron backscatter diffraction pattern collected at the video camera (32) is analyzed to identify representative pixels which reside along Kikuchi bands (78). Backscatter images from subsequent points (62) are rapidly compared (98) with the baseline to detect changes. When changes are not detected, EBSPs are not analyzed. When changes are detected, EBSPs are analyzed to generate new baselines. The resulting collection of analyzed EBSPs are processed (104) to identify microstructure attributes and to characterize defects (64).

28 Claims, 4 Drawing Sheets

METHOD AND APPARATUS FOR IDENTIFICATION OF CRYSTALLOGRAPHIC DEFECTS

TECHNICAL FIELD OF THE INVENTION

The present invention relates generally to material sciences. More specifically, the present invention relates to orientation imaging microscopy and to the analysis of electron backscatter diffraction to detect defects in polycrystalline materials.

BACKGROUND OF THE INVENTION

Polycrystalline materials serve as the basic building blocks for a vast assortment of man-made articles. The properties and behaviors of these materials are determined, at least in part, by the size and shape of the constituent crystallites or grains, the orientation of their crystal lattices, and how the grains are placed to fill space. Accordingly, these attributes of the materials microstructure must be determined in order to understand why certain materials behave as they do, to predict how materials will behave, and to alter or otherwise control material forming and processing techniques to improve specific material properties.

Automated orientation imaging microscopy (OIM) has enabled researchers, material processors, and manufacturers to obtain much valuable microstructure information over a relatively large material sample area. Generally, OIM repetitively bombards selected points of a material sample with a beam of electrons. The electrons interact with a small volume of the material sample at the selected points, and backscatter diffraction patterns form on a phosphor screen near the specimen and may be imaged through a video camera. The video images are called electron backscatter diffraction patterns (EBSPs) or backscatter Kikuchi diffraction (BKD) patterns.

Good quality, high contrast, EBSPs include a number of intersecting, relatively high intensity "Kikuchi" bands generally bordered by thin dark lines. The Kikuchi bands result from electrons being diffracted from various planes in the crystal lattice at the point of bombardment. An abundance of microstructure information, including lattice orientation, may be obtained by analyzing the various parameters of the Kikuchi bands. Sophisticated computer-implemented image processing techniques have been developed to analyze Kikuchi bands from EBSPs taken at numerous points on a material sample and to combine this information into OIM maps which describe a wealth of microstructure information.

Unfortunately, each EBSP may include hundreds of thousands of pixels, and tens of thousands of points on a single material sample may be bombarded with an electron beam to produce tens of thousands of EBSPs. Consequently, an immense number of computer operations must be performed to form a single OIM map. Even with very fast computers, the entire process of forming and analyzing each OIM map takes an undesirably long period of time.

A defect in a material is a relatively small region of a material sample which exhibits microstructure properties that differ from the properties exhibited throughout a larger region near the small region. Thus, examples of defects include grain boundaries, cracks, scratches, voids, plastic deformation, fatigue damage, and the like. In materials science and engineering, defects and the microstructure surrounding defects are often of much interest. Electron bombardment at a defect often yields a low quality EBSP from which Kikuchi bands may be detected with only a low degree of confidence. Consequently, defect information on conventional OIM maps is indirectly inferred from the absence of high confidence microstructure information at particular coordinates on a material sample after an exhaustive and thorough OIM analysis has taken place.

SUMMARY OF THE INVENTION

Accordingly, it is an advantage of the present invention that an improved method and apparatus for identifying crystallographic defects are provided.

Another advantage of the present invention is that defect coordinates are identified without performing a complete microstructure analysis for numerous material sample points that do not reside near a defect.

Another advantage of the present invention is that microstructure information for a large material sample is obtained quickly.

Another advantage of the present invention is that defect information is associated with microstructure attributes in the vicinity of defects.

The above and other advantages of the present invention are carried out in one form by a method of identifying crystallographic defects. The method calls for illuminating a first point on a material sample. A backscatter diffraction image is collected in response to the illumination. A second point is illuminated on the material sample, and a backscatter diffraction image is collected for the second point. The backscatter diffraction images collected for the first and second points are evaluated to determine whether differences between the images exceed a predetermined level. Coordinates of the second point are identified as belonging to a crystallographic defect when the differences exceed the predetermined level.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF THE PREFERRED EMBODIMENTS

Figure 1:
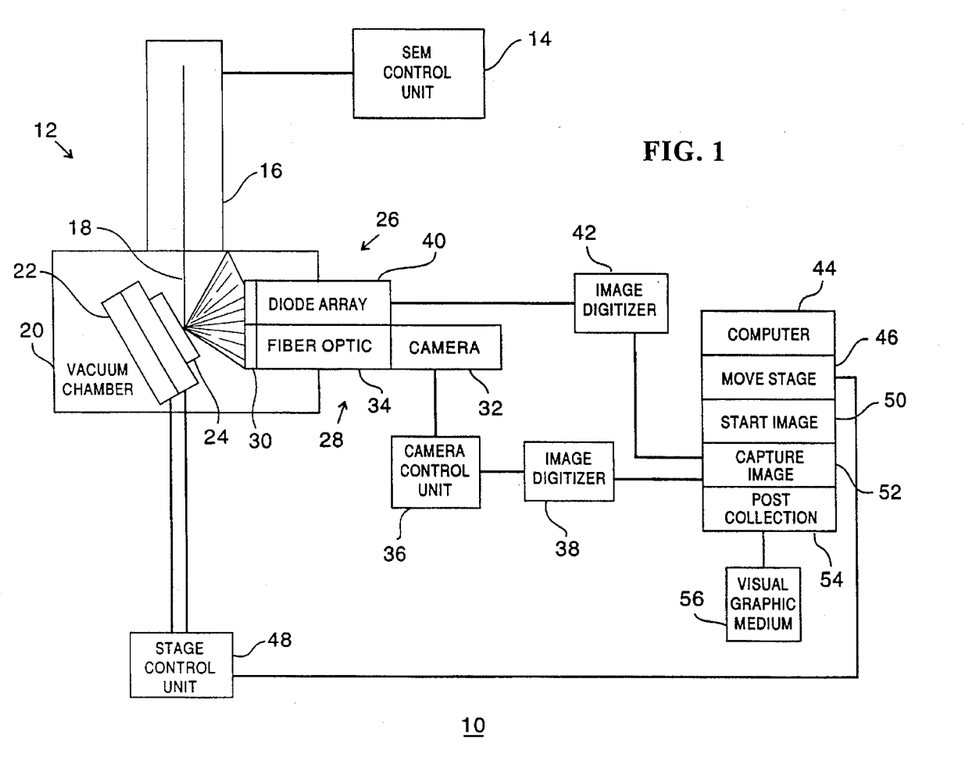
FIG. 1 shows a block diagram of a crystallographic defect and orientation imaging apparatus.

FIG. 1 shows a block diagram of a crystallographic defect and orientation imaging apparatus 10. Imaging apparatus 10 incorporates a conventional scanning electron microscope (SEM) 12. SEM 12 includes a SEM control unit 14 which couples to an electron beam generator 16. Under the direction of control unit 14, beam generator 16 discharges a focused electron beam 18 in a vacuum chamber 20. An adjustable stage 22 is mounted in chamber 20 so that a material sample 24 mounted thereon is bombarded or illuminated by electron beam 18, preferably at an angle of approximately 70° from perpendicular.

An image collection system 26 is positioned within chamber 20 so that a shower of backscatter electrons diffracted from material sample 24 at a high angle from the incident electron beam 18, desirably at around 110°, falls thereon. Image collection system 26 includes a video camera collection device 28 in which a screen 30 coated with a scintillating material couples to a video camera 32 through a fiber optic bundle 34. The screen 30 luminesces in correspondence to the pattern of backscatter diffracted electrons falling thereon. This luminescent image is captured by camera 32, where it is converted to electrical signals, passed through a camera control unit 36, and converted into digital data in an image digitizer 38.

In the preferred embodiment, image collection system 26 additionally includes a diode array 40 having M×N closely positioned diodes, where M and N are integer numbers desirably in the range of three to one hundred. Backscatter diffracted electrons falling on diode array 40 excite various ones of the individual diodes to various degrees, causing diode array 40 to generate electrical signals that describe the pattern and intensity of this excitement. These electrical signals are converted into digital data in an image digitizer 42. Diode array 40 is positioned near phosphor screen 30 so that the geometric relationship therebetween is known. Diode array 40 is included in the preferred embodiment because of its quick response when compared with video camera collection device 28. However, in an alternate embodiment diode array 40 may be omitted, which causes a slight degradation in the number of images which may be processed in a unit of time when compared to the preferred embodiment.

A computer 44 controls the detection of defects in material sample 24. Computer 44 is a conventional computer desirably having as much computing power as is economically practical. Computer 44 includes conventional computer components, including a memory (not shown) which stores programming instructions that define processes carried out by imaging apparatus 10 and which stores data generated by the operation of imaging apparatus 10.

Computer 44 includes a move stage processor block 46 which controls the movement of stage 22 through a stage control unit 48. Through control of stage 22 and electronic steering of electron beam 18, a wide area of material sample 24 may be illuminated by electron beam 18 with backscatter diffraction falling upon image collection system 26. Computer 44 additionally includes a start image processor block 50, which coordinates image collection with electron beam activation. A capture image processor block 52 performs initial image processing and coordinates with move stage processor 46 and start image processor 50 to index subsequent backscatter diffraction images. Capture image processor 52 receives input data from image digitizers 38 and 42 and is discussed in more detail below in connection with FIG. 3. A post collection processor block 54 analyzes data collected from numerous backscatter diffraction images taken from numerous points on material sample 24. Post collection processor 54 is discussed in more detail below in connection with FIG. 6. The output from capture image processor 52 and/or post collection processor 54 drives a visual graphic medium 56, such as a video display terminal, printer, or other device which may serve to convey defect and related microstructure information.

Those skilled in the art will appreciate that processors 46, 50, 52, and 54 implemented within computer 44 need not be separate physical entities but are distinguishable logical entities. With the exception of diode array 40, image digitizer 42, and processors 52 and 54, the components of imaging apparatus are conventional in the art of orientation imaging microscopy and need not be discussed in detail.

Figure 2:
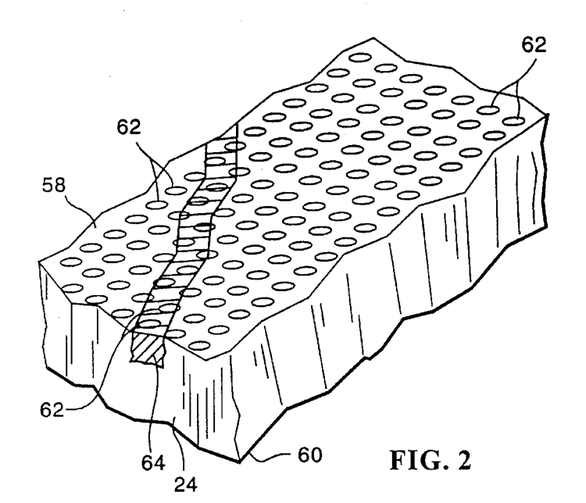
FIG. 2 shows a perspective schematic view of an exemplary portion of a polycrystalline material sample which is subjected to electron bombardment in the imaging apparatus.

FIG. 2 shows a perspective schematic view of an exemplary portion of material sample 24. Material sample 24 has been prepared by making a target surface 58 reasonably parallel to a mounting surface 60, which contacts stage 22 (see FIG. 1). In addition, target surface 58 is reasonably polished to remove scratches. FIG. 2 illustrates numerous points 62 upon target surface 58. Points 62 indicate the locations upon surface 58 that are bombarded with electron beam 18 (see FIG. 1). Points 62 may or may not be noticeable on target surface 58 after completion of scanning. Some sort of backscatter diffraction image is collected from each point 62, as discussed below. Each point 62 represents a small volume of material sample 24, typically around 0.2 μm in diameter. In the preferred embodiment, the field of points may cover a region more than 0,027×0,026 meters. In alternate embodiments, continuous scanning may be performed so that points 62 represent sections of a continuous scan path.

FIG. 2 illustrates points 62 as forming an array with aligned rows and columns, which is a convenient but otherwise unnecessary arrangement for points 62. The spacing between points 62 may vary from application to application, and is desirably a parameter which may be set by an operator prior to scanning material sample 24. Typical values range from less than one μm to one hundred μm. For defect detection, step size (i.e. the distance between points 62) is typically in the lower region of this range so that defects are less likely to be missed. Of course, smaller step size leads to an increased number of images to process for an entire material sample 24, and rapid image processing becomes all the more important.

In addition, FIG. 2 schematically illustrates an exemplary defect 64. Defect 64 may represent a crack, scratch, region of plastic deformation, region of fatigue damage, or even a grain boundary. While different types of defects 64 may exhibit different characteristics, they share the characteristic of having different microstructure attributes from surrounding regions. Thus, the coordinates of a region of changed microstructure coincide with the coordinates of a defect, such as a crack. Different ones of points 62 fall inside and outside of defect 64.

Figure 3:
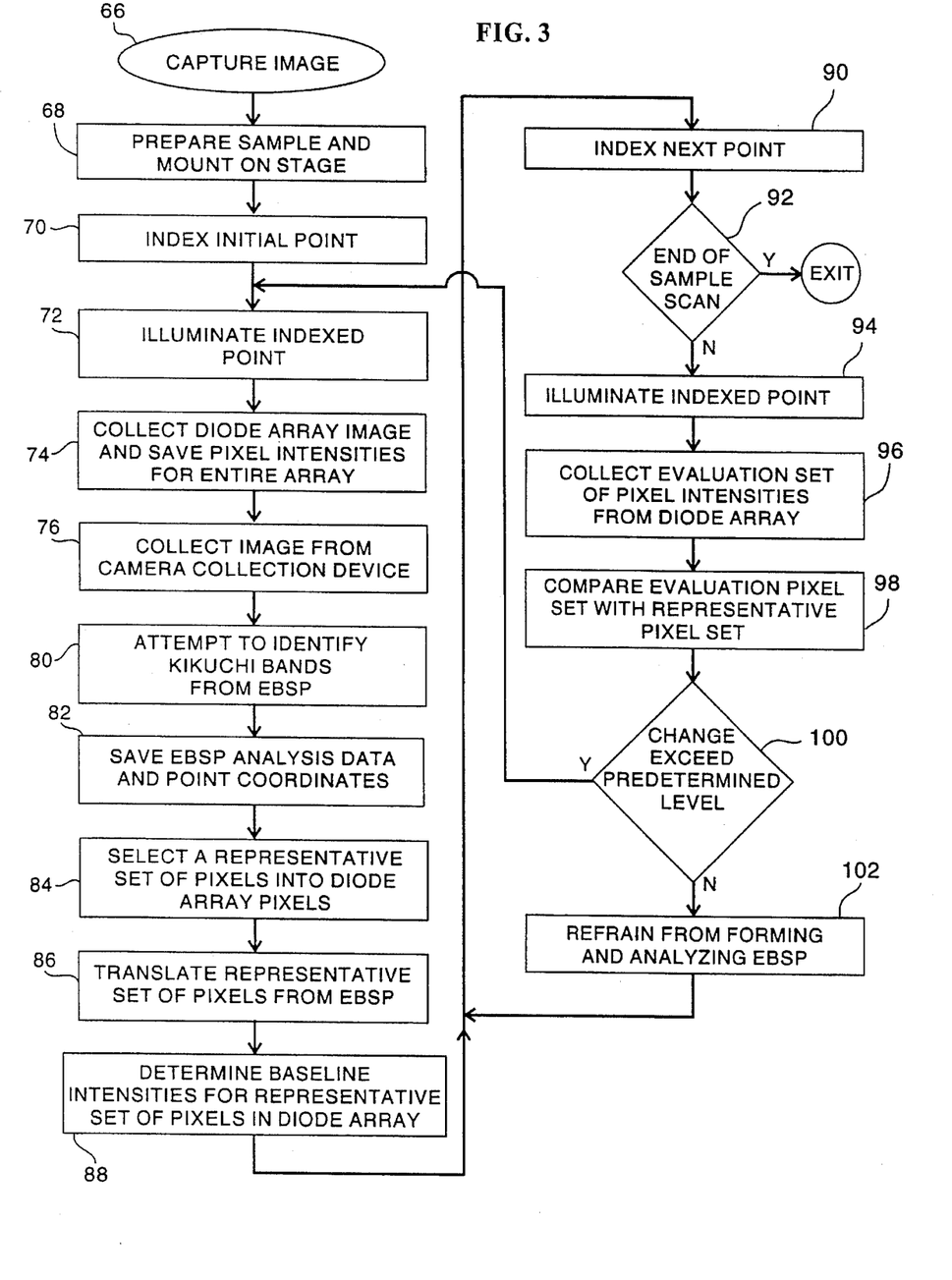
FIG. 3 shows a flow chart of a capture image process performed by the imaging apparatus.

FIG. 3 shows a flow chart of a capture image process 66 performed by imaging apparatus 10 under the control of capture image processor 52 in computer 44. Generally, process 66 collects data from electron backscatter diffraction obtained at various points 62 located in and near defects 64.

Process 66 performs a task 68 to prepare material sample 24 as discussed above in connection with FIG. 2 and to mount sample 24 on stage 22 (see FIG. 1). Task 68 may be performed with human intervention. After task 68, material sample 24 is not moved relative to stage 22 until scanning is complete so that a common coordinate system is used for all points 62 (see FIG. 2) which supply data that identify defects, such as defect 64 (see FIG. 2), and the microstructure of material sample 24 in the vicinity of defect 64.

After task 68, a task 70 moves electron beam 18 to an initial point 62 on material sample 24. By moving electron beam 18 to a point 62, computer 44 controls stage 22 and the electronic steering of electron beam 18 (see FIG. 1) so that electron beam illumination will occur at a desired location on material sample 24. The initial point may be selected to promote any convenient scanning technique. For example, scanning may start in one corner of material sample 24 and illuminate numerous points in a straight line, then numerous parallel lines of points until an entire sample has been scanned. Alternatively, a centrally located point may be first selected and subsequent points may spiral outward therefrom. Desirably, a scanning pattern is selected so that movement of beam 18 between points is quick and so that consecutively scanned points are generally near one another.

After task 70, a task 72 activates electron beam 18 to illuminate or bombard the current point 62. In task 72, the illumination desirably lasts long enough so that an image is obtained from video camera collection device 28 (see FIG. 1). This duration is longer than necessary to obtain an image from diode array 40 (see FIG. 1). Thus, in a task 74 an electron backscatter diffraction image is collected from diode array 40, with pixel intensities from all diodes in the entire array being saved for potential use later.

Figure 4:
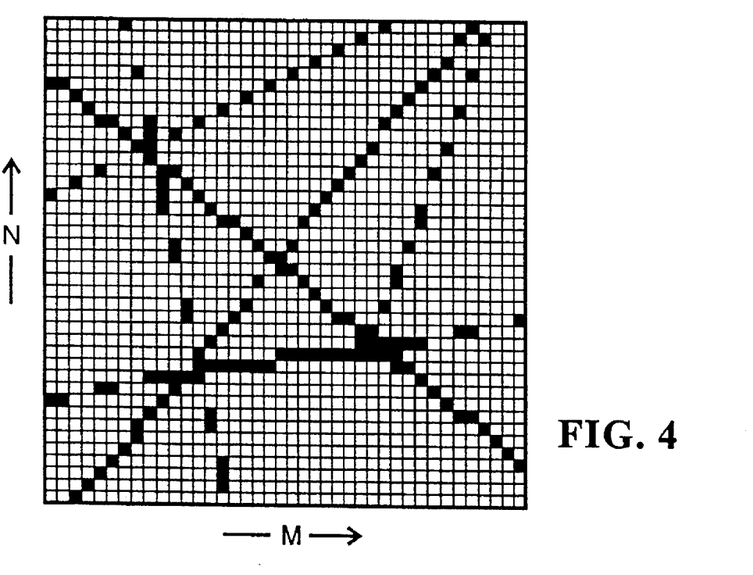
FIG. 4 shows a schematic representation of an exemplary electron backscatter diffraction image collected through a diode array image collection device of the imaging apparatus.

FIG. 4 shows a schematic representation of an exemplary electron backscatter diffraction image collected through diode array 40. Shaded grid locations in FIG. 4 indicate diode array pixels (or individual diodes) reporting a greater intensity. Array 40 may describe its image using up to several thousand individual pixels.

Referring back to FIG. 3, a task 76 collects an electron backscatter diffraction image from video camera collection device 28. This image forms an electron backscatter diffraction pattern (EBSP), also know as a backscatter Kikuchi diffraction (BKD) pattern. The image from video camera collection device 28 may be described using hundreds of thousands of individual pixels.

Figure 5:
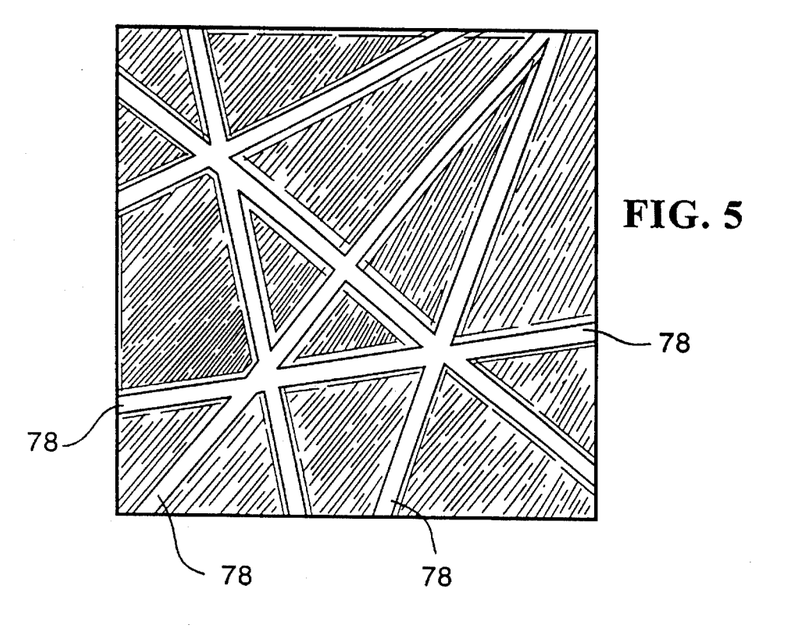
FIG. 5 shows a schematic representation of an exemplary electron backscatter diffraction pattern (EBSP) obtained through a camera image collection device of the imaging apparatus.

FIG. 5 shows a schematic representation of an exemplary electron backscatter diffraction pattern (EBSP) obtained in task 76. FIG. 5 illustrates Kikuchi bands 78 as being higher intensity stripes of varying width, spacing, and orientation. Kikuchi bands 78 intersect each other at various points and are generally bordered by thin lines of lower intensity.

However, FIG. 5 exaggerates the contrast available in a typical EBSP for the sake of clarity. The contrast of the image collected in task 76 will vary depending upon the microstructure of material sample 24 at the point 62 being illuminated. For example, when the illuminated point 62 resides in a crack or scratch, the backscattering direction for electrons can lead through a longer material path before exiting from material sample 24. Consequently, few electrons may exit, and portions or all of the resulting image may be entirely dark. For minor cracks on the order of 50 nm or less and other types of defects, the resulting image may simply exhibit less intensity and poorer contrast than that which results from a point 62 remotely located from a defect.

Referring back to FIG. 3, after task 76 a task 80 attempts to identify the locations of Kikuchi bands 78 (see FIG. 5). Task 80 uses well known algorithms, such as the Hough transform, to identify Kikuchi bands 78. In addition, task 80 may employ other well known image enhancing techniques, such as removing a background before attempting to identify Kikuchi bands 78. Those skilled in the art will understand that task 80 may be a computationally intense operation which requires a significant amount of time to complete.

Moreover, depending upon the contrast available in the EBSP, task 80 may not be entirely successful in identifying Kikuchi bands 78. Thus, locations identified in task 80 may or may not coincide with actual Kikuchi bands 78, depending upon the contrast of the image collected above in task 76. Image contrast may be measured and used to indicate the degree of confidence achieved in task 80.

Next, a task 82 saves the EBSP analysis data and coordinates of the illuminated point 62 for use later by post collection processor 54. Microstructure and crystallographic data are obtained from these data. Since material sample 24 remains fixed on stage 22, the microstructure data will be associated with a coordinate system that likewise identifies defects. Thus, defects are linked to the associated defect microstructure through this coordinate system.

After task 82, a task 84 selects a representative set of pixels from the EBSP data. In the preferred embodiment, the representative set of pixels are aligned relative to one another to extend along the higher intensity regions of the EBSP which are defined by the Kikuchi bands 78 discovered above in task 80. This pattern of Kikuchi bands identifies the underlying microstructure, even without specifying what that microstructure may be.

After task 84, a task 86 translates the representative set of pixels discovered by analyzing the EBSP into a set of pixels in diode array 40. This translation may be performed in response to the geometric relationship between diode array 40 and video camera collection device 28 (see FIG. 1). Thus, task 86 identifies those pixels in diode array 40 where the images of the Kikuchi bands should be formed. FIG. 4 illustrates the representative set of pixels translated to diode array 40 by shaded grid locations.

Next, a task 88 determines baseline intensities for the representative set of pixels in diode array 40. These intensities were recorded above in task 74, along with intensities at pixels which are not included in the representative set of pixels. After task 88, a task 90 moves beam 18 to the next point on material sample 24. The movement of beam 18 is performed in accordance with a scanning algorithm, as discussed above in connection with task 70. After task 90, a query task 92 determines whether the entire material sample 24 has been scanned yet. When the entire sample has been scanned, program control may exit capture image process 66 and proceed, for example, to a post collection process discussed below in connection with FIG. 6.

So long as scanning is not yet complete, a task 94 illuminates the selected point 62 on material sample 24 with electron beam 18 (see FIG. 1). Task 94 needs to activate electron beam 18 for only the short period of time required to collect an image from diode array 40. A task 96 then collects an evaluation set of pixel intensities from diode array 40. The evaluation set corresponds to the representative set determined above in task 86. In other words, the same pixels on diode array 40 where the image of the Kikuchi bands should be formed are evaluated. Other pixels are ignored to reduce processing time.

After task 96, a task 98 compares the intensities of the evaluation set of pixels with the baseline intensities determined above in task 88. The comparison performed by task 98 may be performed on a pixel by pixel basis or may be performed by combining pixel intensities and comparing combined results. After task 98, a query task 100 evaluates the comparison to determine whether the amount of intensity change in the evaluation set of pixels from the baseline intensities exceeds a predetermined level. The predetermined level may be a variable specified by a user. Regardless of the level, when the higher intensity Kikuchi band pixels between different points 62 exhibit little or no change, imaging apparatus 10 concludes that the underlying microstructure has not changed, and that no defect is present at the currently imaged point 62.

As long as no change is detected in task 100, process 66 refrains from forming and analyzing an EBSP, as indicated in a task 102, and program control proceeds back to task 90. At task 90, imaging apparatus 10 moves beam 18 to the next point and the illumination, collection, and comparison tasks repeat. Program control remains in the programming loop which includes tasks 90, 92, 94, 96, 98, 100, and 102 until task 100 detects a change when comparing evaluation pixels in electron backscatter diffraction images against the representative baseline. No EBSPs are collected, analyzed, or saved, but points 62 are illuminated, images are collected, and evaluation pixels are analyzed very quickly.

When task 100 detects a change in images, program control returns to task 72, discussed above. The current point 62, or perhaps another point 62 near the current point 62, will be illuminated again, this time for a duration sufficient to allow an EBSP to be formed through the use of video camera collection device 28. The above-discussed process of collecting the EBSP, analyzing the EBSP to identify Kikuchi bands 78, and determining a new baseline against which to compare future points 62 repeats.

Referring to FIG. 2, when the scanning of points 62 does not encounter defect 64, scanning takes place quickly and redundant EBSPs are not analyzed. When defect 64 is encountered, an image change will be detected and an EBSP will be collected and analyzed. If the EBSP has low intensity or poor contrast and Kikuchi bands 78 cannot be accurately identified, the representative set of pixels may have no actual relationship to Kikuchi bands. Consequently, the subsequent point 62 will most likely be evaluated as yielding a changed image from its baseline. The full analysis, the EBSP mode of operation will continue until image quality improves sufficiently to achieve repeatable results between adjacent points 62.

In the above-discussed alternate embodiment where diode array 40 is omitted, process 66 may be altered from that described above. For example, tasks 74, 86, and 88 may be omitted. Instead, the representative set of pixels may be defined for an EBSP collected for each point 62. While an EBSP is collected through video camera collection device 28 for each point 62, not all EBSPs are fully analyzed or saved. Analysis may be omitted for EBSPs whose evaluation pixels indicate no significant change from previous EBSPs. This too achieves image processing speed improvements over conventional techniques while simultaneously locating defects.

Figure 6:
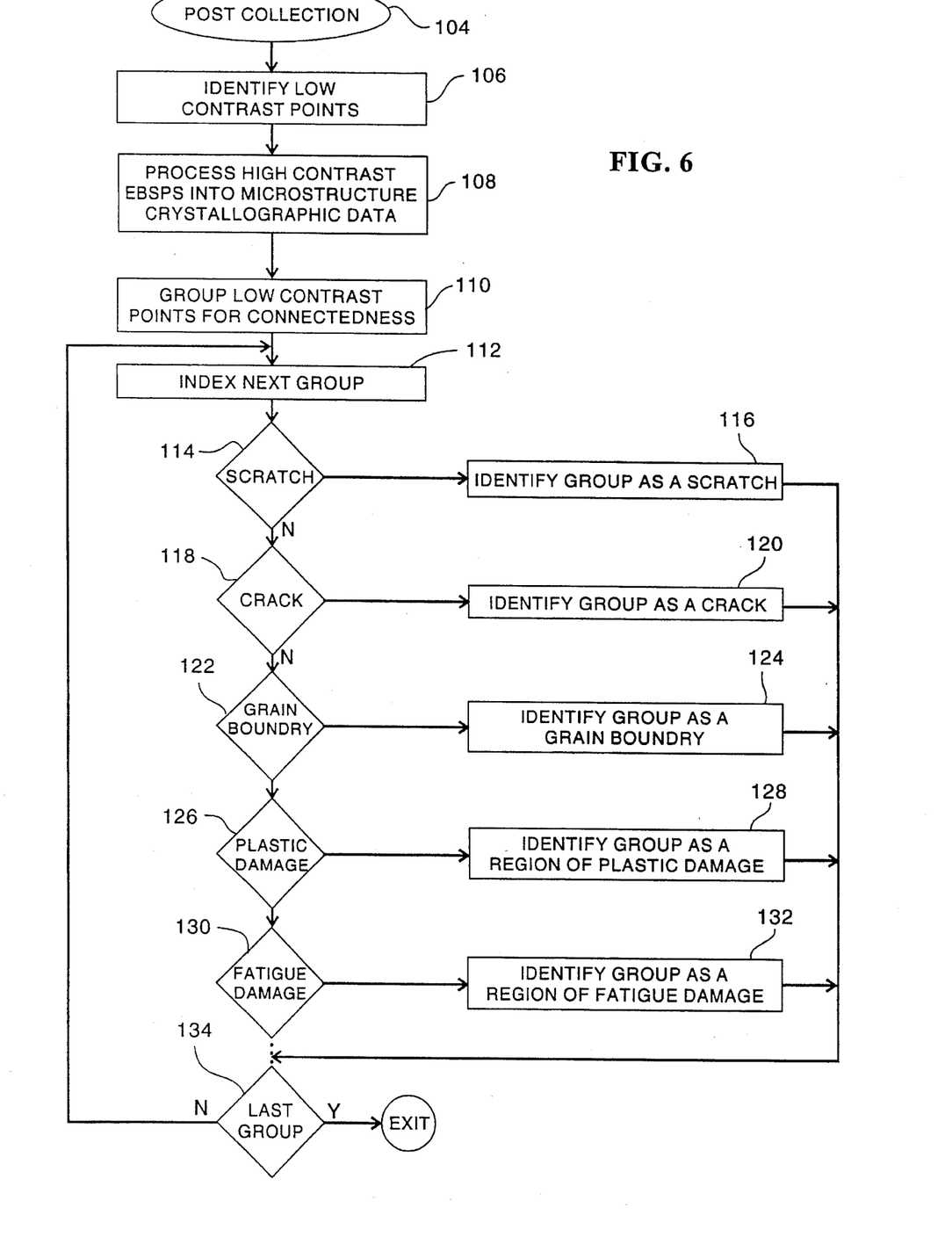
FIG. 6 shows a flow chart of a post collection process performed by the imaging apparatus.

FIG. 6 shows a flow chart of a post collection process 104 performed by imaging apparatus 10 under the control of post collection processor 54. Process 104 is performed after material sample 24 has been entirely scanned. However, nothing requires process 104 to be immediately performed after capture image process 66 (see FIG. 3). Generally, process 104 analyzes the data saved in the numerous iterations of task 82 from process 66 to obtain microstructure and crystallographic data and to classify the defects found through performing process 66. These data describe EBSPs and related coordinates obtained from points 62 where image changes were detected by process 66. Capture image process 66 causes such points 62 to generally reside in and around defects.

Process 104 performs a task 106 to identify the points 62 which yielded low contrast EBSPs. The low contrast EBSPs provide poor data from which microstructure and crystallographic data may be derived. Thus, after task 106 a task 108 processes the higher contrast EBSPs into microstructure and crystallographic data using conventional orientation imaging microscopy (OIM) techniques. Such data include lattice orientation data as an example and indicate coordinates on material sample 24 for the various microstructure attributes.

After task 108, a task 110 groups the points 62 which yielded lower contrast EBSPs for connectedness. In other words, task 110 identifies the points 62 which reside in continuous or near continuous straight or zig-zagged lines or bands. Connected points 62 are grouped together, and non-connected points 62 are grouped separately. Conventional image processing techniques may be employed at task 110.

Next, a task 112 identifies a next group from the groups identified above in task 110. For the first iteration of task 112, a first group is identified. Nothing requires task 110 to identify multiple groups.

After task 112, a query task 114 examines the coordinates, EBSP data, and nearby microstructure data for the current group of points 62 to determine whether a scratch is indicated. Generally, a scratch may be detected by noticing a complete loss of EBSP (i.e. dark, low contrast images) over one to several microns. The lost EBSP points may be connected in a continuous or near continuous, generally straight line. The region adjacent to a scratch may be associated with a loss in diffraction intensity and small to large lattice rotations. If a scratch is detected, a task 116 identifies the group of points 62 as a scratch. A group of points which have been identified as a scratch may be ignored in subsequent material analyses because it may indicate nothing more than imperfect sample preparation.

When task 114 determines that the group is not a scratch, a query task 118 evaluates the group to determine whether it is a crack. Generally, characteristics of a crack and a scratch are similar, except that a crack may not exhibit the straightness exhibited by a scratch. If a crack is detected, a task 120 identifies the group of points 62 as being a crack.

When task 118 fails to identify the group of points as being a crack, a query task 122 evaluates the group to determine whether it represents a grain boundary. A grain boundary may be recognized as forming a closed figure made from narrow line segments. Inside the closed figure a relative consistent lattice rotation may be observed, and outside the closed figure lattice rotations may substantially differ from the internal lattice rotations. If a grain boundary is detected, a task 124 identifies the group of points 62 as being a grain boundary.

When task 122 fails to identify the group of points as being a grain boundary, a query task 126 determines whether the group of points 62 exhibits characteristics consistent with a region of plastic damage. Plastic damage may be identified by a generally oscillating loss in EBSP intensity and visual diffuseness spread over tens or hundreds of microns. Task 126 may investigate points included in other groups in making its determination. If plastic damage is detected, a task 128 identifies the group of points 62 as being a region of plastic damage.

When task 126 fails to identify the group of points as being a region of plastic damage, a query task 130 determines whether the group of points 62 exhibits characteristics consistent with a region of fatigue damage. Fatigue damage may be identified by a loss of EBSP sharpness but not a complete loss of EBSP. The loss in intensity may be associated with local lattice rotations, may extend in a continuous line across the material sample, and may be only a few microns wide. If fatigue damage is detected, a task 132 identifies the group of points as being a region of fatigue damage.

As indicated by ellipsis, process 104 may inquire further to classify the defect identified by the current group of points. Eventually program control encounters a query task 134, which is also performed after each of tasks 116, 120, 124, 128, and 132. Task 134 determines whether the just-evaluated group was the last group for the material sample. If it was not the last group, program control loops back to task 112 to identify the next group and repeat the classification process. When the last group has been classified, program control may exit process 104. Although not shown, the microstructure and defect data may be used in any number of ways, including the forming of maps which may be presented at visual graphic medium 56 (see FIG. 1).

In summary, the present invention provides an improved method and apparatus for identifying crystallographic defects. Defect coordinates are identified without performing an orientation determination for numerous material sample points that do not reside near a defect. Microstructure attribute information for a large material sample is obtained quickly because redundant analyses are avoided. Defect information is associated with microstructure attributes in the vicinity of defects.

The present invention has been described above with reference to preferred embodiments. However, those skilled in the art will recognize that changes and modifications may be made in these preferred embodiments without departing from the scope of the present invention. For example, those skilled in the art can devise alternate processes, task definition, and sequencing than that described herein to achieve substantially the same result. These and other changes and modifications which are obvious to those skilled in the art are intended to be included within the scope of the present invention.

What is claimed is:

1. A method of identifying crystallographic defects comprising the steps of:
   a) illuminating a first point on a material sample;
   b) collecting a backscatter diffraction image in response to said step a);
   c) illuminating a second point on said material sample;
   d) collecting a backscatter diffraction image in response to said step c);
   e) determining whether change between said images collected in said steps b) and d) exceeds a predetermined level; and
   f) identifying coordinates of said second point on said material sample as belonging to a crystallographic defect when said step e) determines that said change between said images exceeds said predetermined level.

2. A method as claimed in claim 1 wherein said step b) comprises the step of attempting to identify Kikuchi bands in an electron backscatter diffraction pattern (EBSP).

3. A method as claimed in claim 1 additionally comprising the step of attempting to identify Kikuchi bands in an electron backscatter diffraction pattern (EBSP) when said step e) determines that change between said images collected in said steps b) and d) exceeds said predetermined level.

4. A method as claimed in claim 3 wherein said attempting to identify step forms said EBSP for a point on said material sample which is proximate said second point.

5. A method as claimed in claim 1 additionally comprising the step of refraining from attempting to identify Kikuchi bands in an electron backscatter diffraction pattern (EBSP) when said step e) determines that change between said images collected in said steps b) and d) does not exceed said predetermined level.

6. A method as claimed in claim 1 additionally comprising the step of positioning first and second image collection devices so that said backscatter diffraction image in said step b) falls upon both of said first and second devices and so that said backscatter diffraction image in said step d) falls upon both of said first and second devices.

7. A method as claimed in claim 6 additionally comprising the step of configuring said first and second image collection devices so that said second image collection device responds to said image more quickly than said first image collection device.

8. A method as claimed in claim 1 wherein:
   said steps b) and d) collect said images at one or more image collection devices which represents each image as a multiplicity of pixels; and
   said method additionally comprises the step of identifying, in response to said step b), a set of pixels associated with said image collected in said step d) to evaluate in said determination of said step e).

9. A method as claimed in claim 8 additionally comprising the steps of:
   g) illuminating a third point on said material sample;
   h) collecting a backscatter diffraction image in response to said step g);
   i) identifying, when change between said images collected in said steps b) and d) exceeds said predetermined level, a second set of pixels which is associated with said image collected in said step h); and
   j) evaluating said second set of pixels associated with said image collected in said step h) to determine whether change between said images collected in said steps d) and h) exceeds said predetermined level, said evaluating step j) occurring when said step e) determines that change between said images collected in said steps b) and d) exceeds said predetermined level.

10. A method as claimed in claim 8 additionally comprising the steps of:
    g) illuminating a third point on said material sample;
    h) collecting a backscatter diffraction image in response to said step g); and
    i) evaluating said set of pixels associated with said image collected in said step h) to determine whether change between said images collected in said steps b) and h) exceeds said predetermined level, said evaluating step i) occurring when said step e) determines that change between said images collected in said steps b) and d) does not exceed said predetermined level.

11. A method as claimed in claim 1 additionally comprising the steps of:
    mounting said sample to a stage prior to said step a); and
    obtaining crystallographic orientation data for said sample while said sample is mounted to said stage and before said sample is significantly moved relative to said stage.

12. A method as claimed in claim 11 wherein:
    said obtaining step comprises the steps of illuminating a third point on said material sample with an electron beam, collecting an electron backscatter diffraction pattern (EBSP) for said third point, and processing said EBSP to identify lattice orientation for said sample at said point; and said step e) takes place more quickly than said processing step.

13. A method as claimed in claim 1 wherein:

said material sample has a crack therein; and said coordinates identified in said step f) coincide with said crack.

14. A method as claimed in claim 1 additionally comprising the step of controlling a visual graphic medium to depict said material sample and said defect.

15. A method of identifying crystallographic defects comprising the steps of:

a) illuminating a first point on a material sample with an electron beam;

b) collecting an electron backscatter diffraction image in response to said step a);

c) forming an electron backscatter diffraction pattern (EBSP) from said electron backscatter diffraction image collected in said step b);

d) identifying a representative set of pixels from said EBSP;

e) illuminating a second point on said material sample with an electron beam;

f) collecting an electron backscatter diffraction image in response to said step e);

g) determining whether intensities at a set of pixels corresponding to said representative set of pixels indicate change between said images collected in said steps b) and f) in excess of a predetermined level; and h) identifying coordinates of said second point on said material sample as belonging to a crystallographic defect when said step g) determines that said change exceeds said predetermined level.

16. A method as claimed in claim 15 additionally comprising, when change between said images collected in said steps b) and f) exceeds said predetermined level, the steps of:

forming a second electron backscatter diffraction pattern (EBSP); and identifying a second representative set of pixels from said second EBSP.

17. A method as claimed in claim 16 wherein said forming step forms said second EBSP for a point on said material sample which is proximate said second point.

18. A method as claimed in claim 16 additionally comprising the step of refraining from forming an EBSP when said step g) determines that change between said images collected in said steps b) and f) does not exceed said predetermined level.

19. A method as claimed in claim 15 additionally comprising the step of positioning first and second image collection devices so that said electron backscatter diffraction image in said step b) simultaneously falls upon said first and second devices and so that said electron backscatter diffraction image in said step f) simultaneously falls upon said first and second devices.

20. A method as claimed in claim 19 wherein:

said forming step c) forms said EBSP from said electron backscatter diffraction image collected at said first image collection device;

said determining step g) evaluates an image collected at said second image collection device; and said second image collection device responds more quickly than said first image collection device.

21. A method as claimed in claim 19 wherein:

said representative set of pixels is associated with said first image collection device; and said set of pixels which is evaluated in said step g) and which corresponds to said representative set of pixels is associated with said second image collection device.

22. A method as claimed in claim 15 additionally comprising the steps of:

i) illuminating a third point on said material sample with an electron beam;

j) collecting a backscatter diffraction image in response to said step i);

k) identifying, when change between said images collected in said steps b) and f) exceeds said predetermined level, a second representative set of pixels which is associated with said image collected in said step j); and l) evaluating a set of pixels associated with said image collected in said step j) and corresponding to said second representative set of pixels to determine whether change between said images collected in said steps f) and j) exceeds said predetermined level, said evaluating step l) occurring when said step g) determines that change between said images collected in said steps b) and f) exceeds said predetermined level.

23. A method as claimed in claim 15 additionally comprising the steps of:

i) illuminating a third point on said material sample with an electron beam;

j) collecting a backscatter diffraction image in response to said step i); and k) evaluating said set of pixels associated with said representative set of pixels to determine whether change between said images collected in said steps b) and j) exceeds said predetermined level, said evaluating step k) occurring when said step g) determines that change between said images collected in said steps b) and f) does not exceed said predetermined level.

24. A crystallographic defect and orientation imaging apparatus comprising:

an electron beam generator;

a stage upon which a material sample may be mounted to receive electron beam illumination from said electron beam generator;

an image collection system positioned to detect electron backscatter diffraction resulting from illuminating points of said stage-mounted material sample with said electron beam; and image processing means, coupled to said image collection system, for identifying a representative set of pixels from an electron backscatter diffraction image collected for a first point on said stage-mounted material sample and for comparing said representative set of pixels with an evaluation set of pixels taken from an electron backscatter image collected for a second point on said stage-mounted material sample to determine whether said second image has changed from said first image.

25. A crystallographic defect and orientation imaging apparatus as claimed in claim 24 wherein said image collection system comprises:

a first image collector positioned to detect electron backscatter diffraction resulting from illuminating points of said stage-mounted material sample with said electron beam; and a second image collector positioned to detect electron backscatter diffraction resulting from illuminating points of said stage-mounted material sample with said electron beam.

26. A crystallographic defect and orientation imaging apparatus as claimed in claim 25 wherein:

said representative set of pixels is selected from an image collected at said first image collector; and said evaluation set of pixels corresponds to said representative set of pixels and is selected from an image collected at said second image collector.

27. A crystallographic defect and orientation imaging apparatus as claimed in claim 25 wherein said second image collector has a quicker response time than said first image collector.

28. A crystallographic defect and orientation imaging apparatus as claimed in claim 24 wherein said image processing means is configured so that:

said evaluation set of pixels is identified in response to said representative set of pixels; and said image processing means is configured to compare said representative set of pixels with said evaluation set of pixels more quickly than it identifies said representative set of pixels.

* * * * *